United States Patent
Susi et al.

(10) Patent No.: US 6,277,081 B1
(45) Date of Patent: Aug. 21, 2001

(54) ANESTHETIC GAS DETECTION APPARATUS

(75) Inventors: Roger Susi, Winter Park; Arthur R. Weeks, Oviedo; David Hefele, Winter Springs, all of FL (US); John Moore, Broken Arrow, OK (US)

(73) Assignee: Invivo Research, Inc., Orlando, FL (US)

( * ) Notice: Subject to any disclaimer, the term of this patent is extended or adjusted under 35 U.S.C. 154(b) by 0 days.

(21) Appl. No.: 09/313,414

(22) Filed: May 18, 1999

(51) Int. Cl.[7] .................................................. A61B 5/08
(52) U.S. Cl. ............................................. 600/532; 250/345
(58) Field of Search .................................. 600/532, 529; 250/339.13, 343, 345, 339.02

(56) References Cited

U.S. PATENT DOCUMENTS

| | | | |
|---|---|---|---|
| 4,069,420 | * | 1/1978 | Ross ....................................... 600/532 |
| 4,180,734 | * | 12/1979 | Gedeon ................................. 600/532 |
| 4,549,080 | | 10/1985 | Baskins . |
| 4,692,621 | | 9/1987 | Passaro . |
| 4,998,018 | * | 3/1991 | Kurahashi et al. ................... 600/532 |
| 5,081,998 | * | 1/1992 | Yelderman et al. .................. 600/532 |
| 5,095,913 | * | 3/1992 | Yelderman et al. .................. 600/532 |
| 5,130,544 | * | 7/1992 | Nilsson ................................. 600/532 |
| 5,296,706 | * | 3/1994 | Braig .................................... 600/532 |
| 5,726,450 | | 3/1998 | Peterson . |
| 5,801,384 | * | 9/1998 | Kirchhevel .......................... 600/532 |
| 5,900,635 | * | 5/1999 | Weckstrom .......................... 600/532 |
| 5,932,877 | * | 8/1999 | Braig et al. ......................... 600/532 |
| 6,001,064 | * | 12/1999 | Weckstrom .......................... 600/532 |
| 6,039,697 | * | 3/2000 | Wilke et al. ......................... 600/532 |

OTHER PUBLICATIONS

Copy of european search report, dated Apr. 9, 2000.

* cited by examiner

Primary Examiner—John P. Lacyk
Assistant Examiner—Brian Szmal
(74) Attorney, Agent, or Firm—Hopgood, Calimafde, Judlowe & Monodolino LLP

(57) ABSTRACT

An apparatus is provided for detecting each of the five known anesthetic agents, $CO_2$, and $N_2O$ when monitoring a patient's respiratory gas stream during anesthesia. A source of infrared radiation emits the infrared tight through a gas stream and onto the infrared detector/sensor. The detector may contain ten analytical channels, each channel containing an independent infrared detector and a specific bandpass infrared filter which only permits certain wavelengths of the infrared radiation to reach the respective infrared detector. One of the channels is a blocked detector which serves as the reference point. A calibration and processing means is also provided to compensate for factors such as offset voltage, cross coupling, wideband changes and thermal drifts which may affect the accuracy of the gas measurements.

15 Claims, 6 Drawing Sheets

ANESTHETIC GAS DETECTION APPARATUS

TECHNICAL FIELD

This invention relates to an apparatus for detecting and measuring the concentration of various unknown gases. In particular, this system may be used to detect and measure the concentrations of $CO_2$, $N_2O$, and five anesthetic agents in a respiratory gas stream.

BACKGROUND

In order to safely administer anesthetic gases to a patient under anesthesia, anesthesiologists need to be able to monitor the concentration of certain gases which patients inhale and exhale to prevent the risk of supplying too much or too little gas. Carbon dioxide ($CO_2$) is not administered, but it and the administered anesthetic gases nitrous oxide ($N_2O$), halothane, enflurane, isoflurane, sevoflurane, and desflurane are monitored. These anesthetic gases may be administered as a single agent gas, or as a mixture of agent gases.

Because expired $CO_2$ is a reliable indicator of the carbon dioxide concentration in the arterial blood, the concentration of expired $CO_2$ is often the most critical of the gases to observe. This supervision helps to prevent excess $CO_2$ from being delivered to the patient, by preventing malfunctions in the anesthetic breathing apparatus.

With the help of modern technology, gas analyzers which utilize infrared radiation have been developed to measure the concentration of $CO_2$ and the anesthetic gases. These gas analyzers take advantage of the known infrared absorption characteristics of $CO_2$ and the anesthetic gases to determine which gases are present. In other words, in a typical gas analyzer, an infrared light would be emitted through a respiratory gas stream in the main (or side) airway, and onto an infrared sensor/detector device which contain certain infrared bandpass filters and a set of thermopiles to ultimately determine the concentration of carbon dioxide or any of the anesthetic gases. For convenience purposes, each combination of an infrared bandpass filter and its respective thermopile will be referred to as a "channel". In this respect, a "channel" thus does not define an actual physical pathway, but rather, is an imaginary pathway arbitrarily defined as in the previous sentence in order to easier describe the invention herein.

One example of such analyzers includes that disclosed in U.S. Pat. No. 5,081,998 entitled OPTICALLY STABILIZED INFRARED ENERGY DETECTOR (the disclosure of which is incorporated herein by reference). As shown in FIG. 1, this analyzer uses pairs-of thermopiles connected in series opposed relation, with the first and second thermopiles of each pair located next to each other, whereby each thermopile is preceded by an optical bandpass or a neutral density filter to permit different infrared radiation wavelengths to reach each thermopile in the pair. This resulting difference in output is then used to eliminate the effects of background thermal noise. However, difficulties were encountered due to the space limitations in trying to arrange six or more independent analytical channels to detect additional anesthetic gases over a restricted mounting area.

This space arrangement problem was apparently improved upon in the apparatus disclosed in U.S. Pat. No. 5,296,706, entitled SHUTTERLESS MAINSTREAM DISCRIMINATING ANESTHETIC AGENT ANALYZER (the disclosure of which is incorporated herein by reference). As shown in FIG. 2, this apparatus uses a first and second thermopile connected in a "parallel opposed" fashion for each independent detector channel. In other words, there are two thermopiles for every detector channel: the first thermopile located in the path of the incident light and the second thermopile shielded from all incident light and located directly behind the first. The purpose of the second thermopile is to produce reference output representative of ambient temperature transients. Upon detection of carbon dioxide and the anesthetic gases, the concentrations of the gases are then calculated using a second order polynomial equation having cross product terms.

The present inventors have found that it was difficult to construct a sensor with seven to ten channels, each with a reference detector connected in a parallel opposed manner directly behind its corresponding infrared detector. The present inventors also found that the use of large order polynomials to calibrate and compensate the measurement was difficult to accomplish.

SUMMARY OF THE INVENTION

It is therefore an object of this invention to provide an improved anesthetic gas detection apparatus suitable for measuring carbon dioxide and more than five anesthetic gases in a respiratory gas stream.

It is another object of this invention to provide an improved anesthetic gas detection apparatus in which only one blocked detector reference detector is used as a reference point for ambient temperature transients.

It is still another object of this invention to provide an improved anesthetic gas detection apparatus which uses a novel calibration process to compensate for errors such as thermal drifts and cross coupling when detecting carbon dioxide and the anesthetic gases.

It is yet another object of this invention to provide an improved anesthetic gas detection apparatus which uses a novel processing means to determine the concentration of carbon dioxide and the anesthetic gases.

Still a further object of the present invention is to provide a durable, reliable, and economical anesthetic gas detection apparatus for use with patients under anesthesia.

Thus, the present invention overcomes the above mentioned problems in the art by using the output of a single blocked detector as a reference point for any ambient temperature transients. This novel aspect of the invention eliminates the need to have a corresponding reference infrared detector for each independent infrared detector.

In the preferred embodiment, this apparatus comprises:

a source of infrared radiation for illuminating the gas conduit;

a plurality of independent infrared detectors, each with an infrared bandpass filter positioned before the detector to permit only infrared radiation of a particular wavelength to reach each respective infrared detector;

one or more reference infrared detectors, each with an infrared bandpass filter positioned before the detector to permit only infrared radiation of a particular wavelength to reach each respective reference infrared detector;

a blocked detector infrared detector, with an opaque filter to prevent substantially all infrared radiation from reaching the blocked detector infrared detector; and processing means for thermally correcting each independent infrared detector output by algebraic removal of a scaled version of a channel's output and the blocked detector infrared detector from the output of each independent infrared detector.

Since each gas will absorb different wavelengths of the infrared radiation, each infrared filter preceding a detector element is designed to only allow selected wavelengths of the infrared radiation to pass through the filter.

Another novel aspect of this invention is the process by which the sensor is calibrated and the gas concentrations are determined. Such a method, in accordance with a preferred embodiment of the invention, may comprise the steps of:

measuring the voltage across each individual thermopile, measuring and compensating for the effects of certain factors such as offset voltage, wideband and thermal changes, and cross coupling, which may distort the accuracy of the thermopile measurements;

determining the concentration of the selected gases based on the results of the calibration process; and zeroing the system at predetermined intervals.

By using the novel calibration and concentration determination process of this invention, accurate results can be obtained when determining the concentration of the various gases in this system since the factors which would distort such measurements are accounted for. Such method will be further described below.

BRIEF DESCRIPTION OF THE DRAWINGS

The objects and advantages of the invention will become more apparent and more readily appreciated from the following detailed description of presently preferred exemplary embodiments of the invention taken in conjunction with the accompanying drawings, of which.

DETAILED DESCRIPTION OF THE INVENTION

Figure 1:
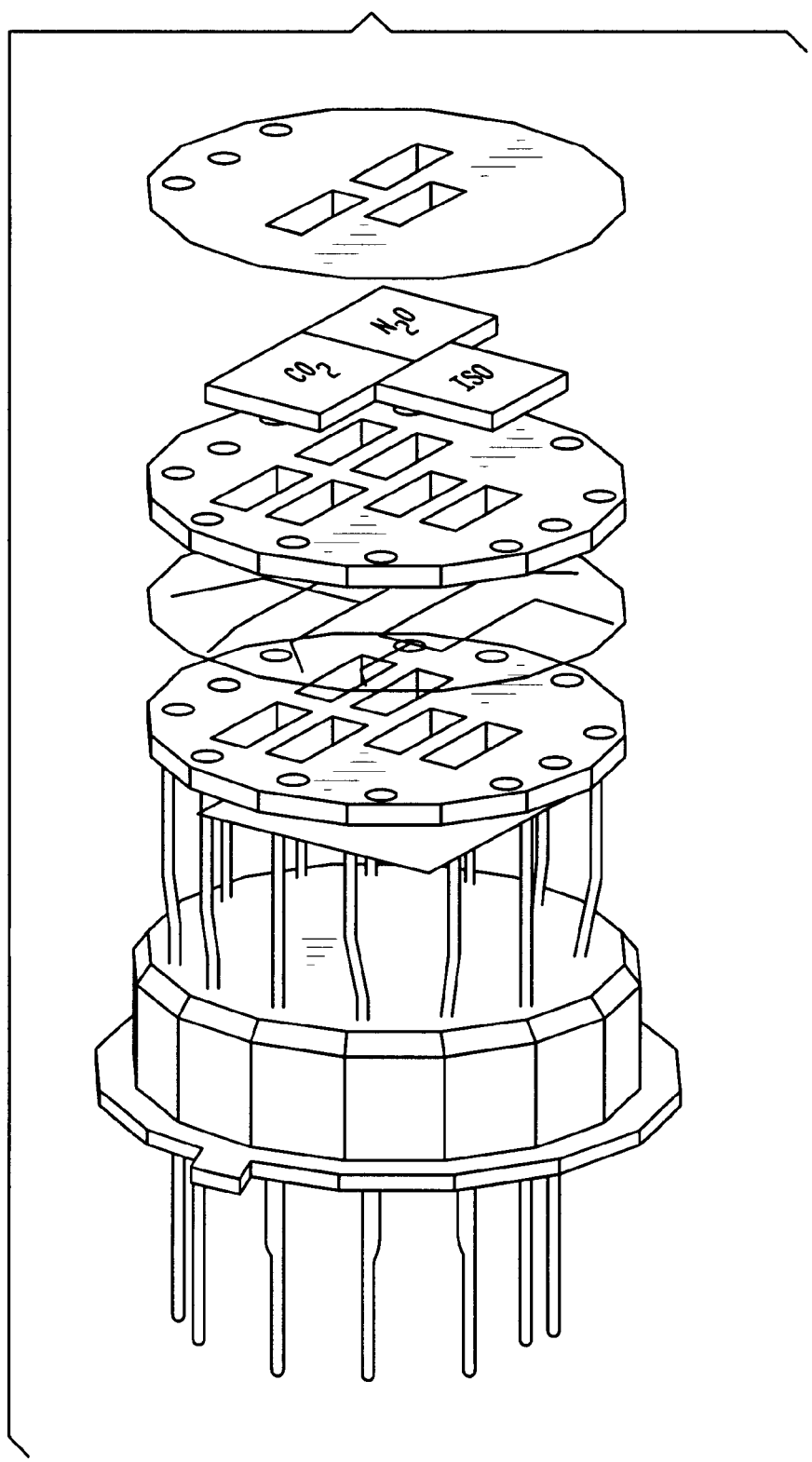
FIG. 1 is an exploded view of a prior art illustrating the pairs of thermopiles, connected in series, of the infrared detector.
Figure 2:
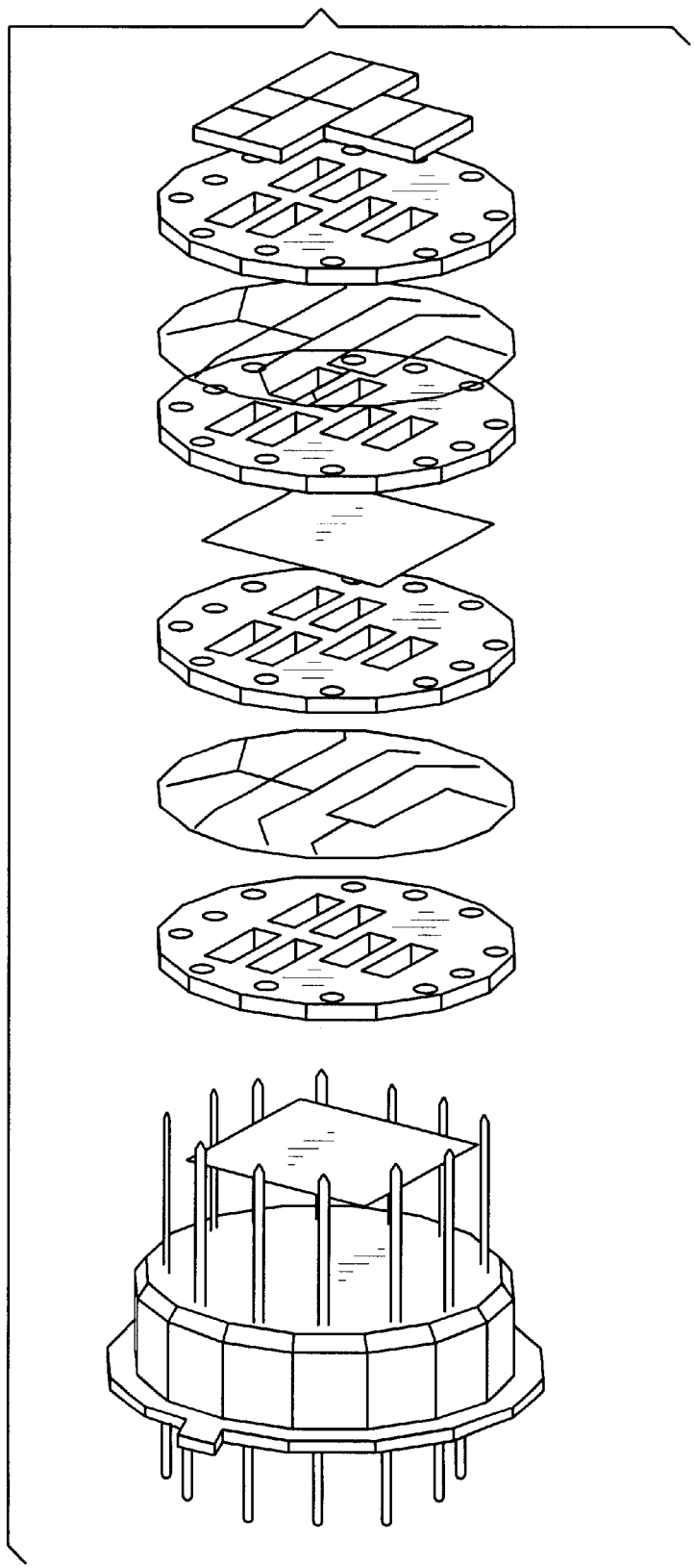
FIG. 2 is an exploded view of a prior art illustrating the "parallel opposed" connection of thermopiles of the infrared detector.

Turning now to the drawings, FIG. 1 illustrates a prior art infrared detector in which sets of pairs of thermopiles are connected in series. These thermopiles can be rearranged in a parallel fashion as in FIG. 2 to increase the number of anesthetic gases that can be detected. However, as described before, this space arrangement is also not without its limits and difficulties.

Figure 3:
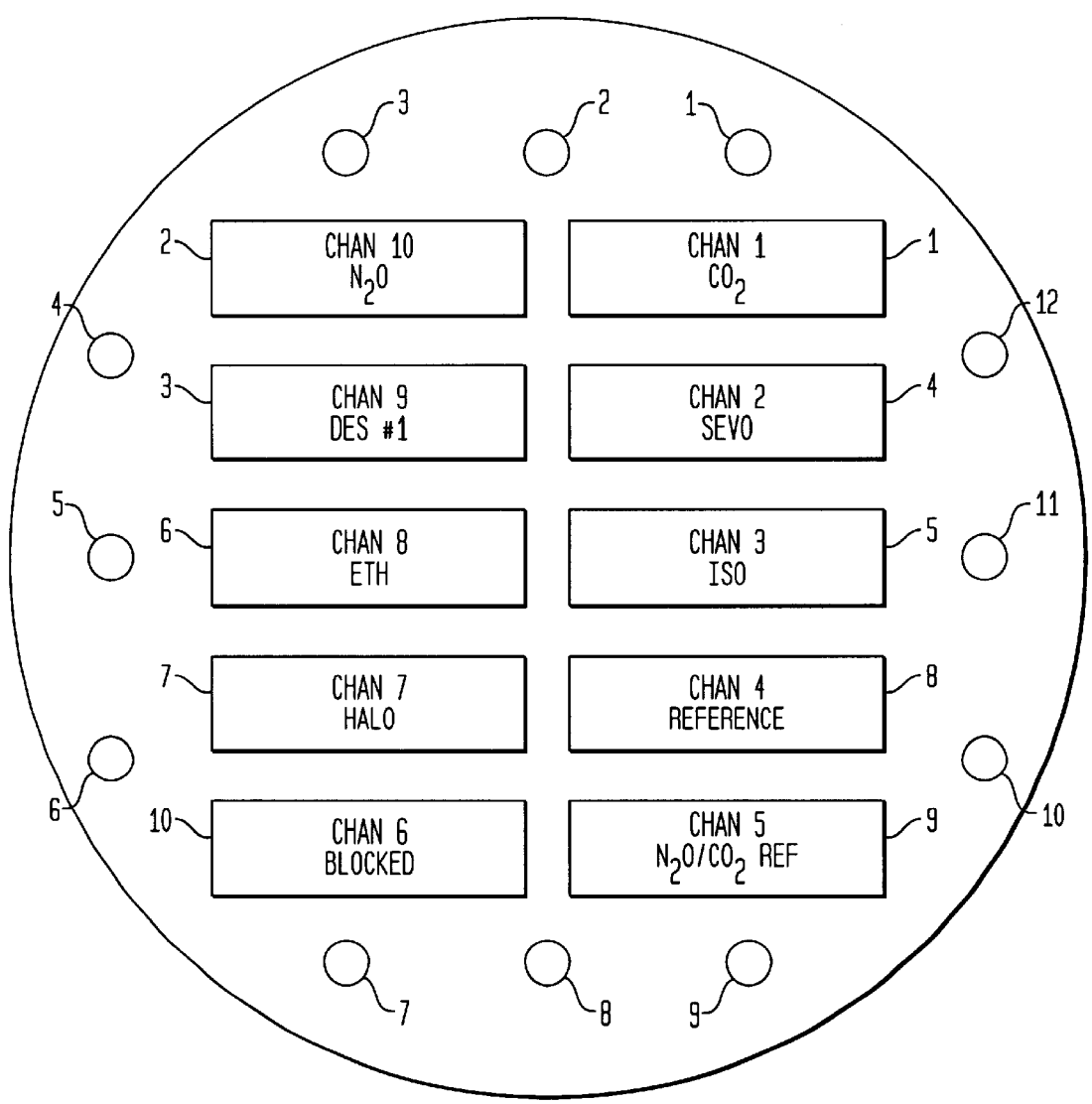
FIG. 3 is a top view of the preferred embodiment of the ten channels located within the infrared detector portion of the gas detection apparatus in accordance with the principles of the present invention.

As shown in FIG. 3, the preferred embodiment of the invention may contain ten channels: a $CO_2$ channel (1), a $N_2O$ channel (2), five agent channels for each of the five known anesthetic agents, namely desflurane (3), sevoflurane (4), isoflurane (5), enflurane (6), and halothane (7), two reference channels (8, 9), and a blocked detector (10). Although $N_2O$ is also an anesthetic gas (or agent), for purposes of describing the invention $N_2O$ will be referred to separately from the other five anesthetic gases. As mentioned earlier, each one of these channels comprises a filter (11–20), a detector element thermopile, (21–30) and preferably an amplifier to amplify the voltage signal coming of the detector. Thought the singular term "filter" will be used throughout this specification, it is to be understood that the "filter" may comprise a plurality of filter elements selected to pass a relatively narrow bandwidth of light to the detector. Each thermopile develops a voltage difference across it when infrared radiation is incident upon the bimetallic detector junction. A thermistor (31) for taking separate operating temperature measurements may also be mounted onto the same surface as the detectors.

Also provided is an infrared source (33) to emit infrared radiation through the respiratory gas stream and onto the detection system. Typically, the infrared source (33) is a heater at approximately 350° C. (e.g., ±20°C.). The respiratory gas stream would be carried inside a gas conduit (35) connected to a patient's airway. Because anesthetic gases absorb certain wavelengths of the infrared radiation and pass others, a voltage decrease develops across a detector when absorption occurs. It is this voltage change which is ultimately utilized by the invention to detect the presence or absence of a gas.

Since each gas will absorb different wavelengths of the infrared radiation, a bandpass infrared filter (32) is placed over a detector element (34) which will only allow certain wavelengths of infrared radiation to pass through the filter. In the seven independent detectors, or analytical channels (1–7), for detecting $CO_2$, $N_2O$, and the five agents, the respective bandpass filters (11–17) will only pass wavelengths of the infrared radiation that is absorbed by the particular gas which we wish to detect onto the respective thermopile (21–27).

On the other hand, for the two reference detectors (8, 9), the respective bandpass filters (18, 19) will only pass wavelengths of the infrared radiation that is not absorbed by the particular interested gas onto the respective thermopile (28, 29). While the reference detectors (8, 9) may be used for any of the seven gases present, one of the reference detectors is typically designated as an agent reference channel (8), and the other reference detector is usually designated as a $CO_2/N_2O$ reference channel (9). Thus by way of example, the bandpass filter for the $CO_2/N_2O$ reference detector (19) will only allow infrared radiation absorbed by the other five anesthetic agents to pass through it.

As for the blocked detector (10), an opaque filter (20) is placed before the blocked detector thermopile (30) to essentially block all infrared radiation from reaching this thermopile. This blocked detector (10) serves as the reference point to correct for the effect of thermal drifts. Instead of having a corresponding reference point detector for each independent infrared detector, the present inventors have found that the output of a single blocked detector (10), scaled appropriately, can be used to thermally compensate the output of the independent measurement channels. By only using a single blocked detector (10), the present invention eliminates the complications and difficulties inherent in structuring a second corresponding thermopile (in parallel or in series) for each independent thermopile.

Another important aspect of this invention is the process by which the sensors are calibrated so that an accurate determination of the concentration of the interested gas may be achieved. Calibration begins once the sensor assembly has reached a steady state operating temperature of approximately 50° C. to 60° C. Best results are obtained after substantially complete warm-up when the operating temperature of substantially the entire system environment is stable.

Once a stable operating temperature has been achieved, calibration begins with measuring and eliminating the offset voltages of each of the ten detector elements. Each detector has a unique D.C. offset voltage value (also called a "no signal" or "dark" offset) that is present in the absence of any infrared radiation, typically 2 to 6 times the signal. The D.C. offsets in the detector elements are caused by the ambient heat that is transferred to the detector elements. These offsets are determined at calibration time by blocking all infrared radiation from the detector for a short period (e.g., no more than about 3 to about 5 seconds) and then measuring the voltages for each detector element. This small period of time is needed to prevent the overall temperature of the detector from changing significantly. The value of these D.C. offset voltages ($V_{DC\ Offset}$) must then be subtracted from the value of the voltages ($V_{Channel\ with\ a\ DC\ offset}$) from all ten detectors, with generally about ten percent of the value of the measured D.C. offset voltage left to reduce the possibility of the corrected detector voltage value ($V_{channel\ with\ DC\ offset\ corrected}$) from becoming negative.

$$V_{channel\ with\ DC\ offset\ corrected} = V_{channel\ with\ a\ DC\ offset} - (0.9)V_{DC\ Offset} \quad \text{Equation 1}$$

Measurement and elimination of these offset voltages helps to improve the overall modulation of a channel for a given gas concentration. By "modulation" is meant changes in detector output for a fixed gas concentration.

The next step in the calibration process is referred to as the "primary thermal compensation" of the detector. This corresponds to calibrating each of the detector outputs (desflurane, sevoflurane, isoflurane, enflurane, halothane, agent reference, $CO_2$ reference, and blocked detector) to produce an accurate agent value for each of the seven gas channels (desflurane, sevoflurane, isoflurane, enflurane, halothane, $CO_2$, and $N_2O$). Primary thermal compensation is accomplished by using three detectors: the blocked channel detector (30), the agent reference detector (28), and the $CO_2/N_2O$ reference detector (29). The blocked detector (10) has an opaque filter (20) that blocks all infrared radiation. The agent reference detector and $CO_2/N_2O$ reference detectors (8, 9) have filters (18, 19) that only pass infrared radiation at wavelengths that are not absorbed by the agent gases and the $CO_2/N_2O$ gases respectively.

As part of the primary thermal compensation, the blocked detector contains a long term thermal drift due to the detector itself changing its thermal operating point. In the actual analytical stage, the voltages ($V_{Channel}$) of all the independent and reference detectors (the seven gases and two references) are corrected for this long term thermal drift by subtracting the product of the blocked detector's voltage ($V_{block}$) multiplied by a properly selected scale factor ($ScaleFactor_{channel}$):

$$V_{channel} = V_{channel\ with\ DC\ offset\ corrected} - (ScaleFactor_{channel})(V_{block}) \quad \text{Equation 2}$$

At this calibration stage, the above equation is used to calculate the scale factor, which is important because each detector behaves slightly differently from the other detector elements. By properly calculating the scale factor, the correct amount of the blocked detector's value can be subtracted from the agent, $CO_2$, $N_2O$, and reference detectors' outputs.

A preferred calibration technique was developed that will determine the scale factor for each gas channel. Because desflurane introduces more thermal change in the detectors than any other agent, 18 volume percent of desflurane is used to change the temperature of the sensor. A pneumatic valve is used to switch between 18% desflurane and air at a rate of 1 cycle every 500 seconds (250 seconds of fresh air, then 250 seconds of desflurane). This produces a modulation in the base signal levels of the agent, $CO_2$, $N_2O$, reference, and blocked detectors. A scale factor for each gas detector channel is adjusted to minimize the change in the difference between the gas detectors and the blocked detector.

After performing primary thermal compensation, the effects of temperature changes in the heater and detector channel filters must now be removed. This is referred to as "secondary thermal compensation". Secondary thermal compensation is accomplished by dividing the value of the voltages of the $CO_2$, $N_2O$, or anesthetic agent gas detectors ($V_{channel}$) by the value of the voltages of their corresponding reference detectors ($V_{reference}$). This results in a more accurate voltage reading ($R_{channel}$) of each gas because the effect of any temperature fluctuation is thereby removed.

At thermal equilibrium, any change in temperature will be common to all of the detector filters. Therefore, the voltage changes caused by the temperature changes ($V_{ThermalNoise}$) will be common to all channels and thus we may assume that the thermal noise for an agent or $CO_2$ channel is the same as the thermal noise for the respective agent or $CO_2$ reference channel.

$$R_{channel} = \frac{(V_{channel})(V_{ThermalNoise})}{(V_{reference})(V_{ThermalNoise})} = \frac{V_{channel}}{V_{reference}} \quad \text{Equation 3}$$

Hence, the $V_{ThermalNoise}$ cancels.

The $CO_2$ and $N_2O$ detector voltage values are divided by the $CO_2/N_2O$ reference detector voltage value, the agent detector voltage values are divided by the agent reference voltage value.

It has been found that, depending upon the manufacture of the filters, the agent reference channel, though sufficient, is not necessarily the best possible channel to use as a reference for the agent detectors when calibrating for secondary thermal compensation. This is because of variances in manufacturing technique and quality among different manufacturers of filters. It is found, for example, that when using filters supplied by Takos, Inc. (Nesonset, N.Y.), better results are obtained if the agent channel voltages are divided by the sevoflurane channel voltage. The sevoflurane detector channel voltage is then divided by the agent reference channel voltage. It is believed that the reason for this is that this particular make of filters are engaged in a cross-coupling between the sevoflurane channel and the other agent channels. By using the sevoflurane channel, it is believed that this cross-coupling effect is eliminated.

Dividing the agent detectors of isoflurane, halothane, and enflurane by the sevoflurane detector reduces cross-coupling effect of sevoflurane on these agent channels. An alternative means of reducing the cross-coupling is by choosing different filters or filter designs, in which case all agent channels could be divided by the agent reference.

The practitioner should know, then, that the preferred method is to experiment with division of each combination of three agent channel voltages by the remaining fourth agent channel voltages to see if better results can be obtained than from division by the agent reference channel voltage itself. If so, then the agent channel chosen as a reference is then calibrated by using the agent reference channel itself.

Which agent would be best varies with the kind and quality of the filters chosen. This method is not required, however, and the practitioner is free to simply divide all the agent channel voltages by the agent reference channel voltage to achieve satisfactory results.

The normalized ratios for each of the seven gas channels ($NR_{channel}$) are then obtained by dividing each gas channel's voltage after secondary thermal compensation ($R_{channel}$) by the value of the gas channel's voltage ($R_{atm}$) when no anesthetic agent gas is present (e.g., in the presence of atmospheric air):

$$NR_{channel} = R_{channel}/R_{atm} \qquad \text{Equation 4}$$

Next, the normalized voltage ratios for each channel ($NR_{channel}$) are adjusted to ensure that the modulation level in each channel is the same. To do this, a pure sample of each gas is placed into the targeted stream and the maximum modulation is found by applying the maximum concentration of each agent individually to each sensor and measuring the total change in the normalized ratio for each channel. The two gas concentrations that produce the largest change in an individual channel are then determined. Their corresponding normalized ratios are then multiplied together to yield the combined gas normalized ratio, $NR_{2\text{-}channel}$. This process is repeated for each of the agent, $CO_2$ and $N_2O$ channels.

Each of the normalized ratios are then scaled so that the maximum modulation due to the two gases (that showed the maximum modulation) combined is equal to 75 percent. This is done via the equation:

$$NR_{channel\ corrected} = 1 - RG_{channel}(1 - NR_{channel}) \qquad \text{Equation 5}$$

where $RG_{channel} = 0.75/(1 - NR_{2\text{-}channel})$ and is referred to as the modulation coefficient (or ratio gain adjustment value) and $NR_{channel\ corrected}$ is the modulation-adjusted normalized voltage ratio for each respective gas channel.

Now that normalized ratios are available for the $CO_2$ and $N_2O$ channels and the five agent channels, we can finally determine the volume percentages of the $CO_2$ and $N_2O$ that exist using the equations:

$$\%CO_2 = \phi CO_2 CO_2^{-1}(NRCO_2) \qquad \text{Equation 6a}$$

$$\%N_2O = \phi N_2 ON_2 O^{-1}(NR_{N2O}) \qquad \text{Equation 6b}$$

where $\phi CO_2 CO_2^{-1}$ and $\phi N_2 ON_2 O$ represent the equations that map a normalized voltage ratio to a gas volume percentage or concentration and $NRCO_2$ and $NRN_2O$ represent the modulation adjusted normalized voltage ratios for carbon dioxide and nitrous oxide respectively.

Since $CO_2$ and $N_2O$ will have an effect on each other's channel, this cross coupling of the $CO_2$ and $N_2O$ channels must be eliminated by subtracting the effect that each gas has on the other channel. The amount of channel cross coupling, cross ($\%Gas_1$), $\%Gas_2$), is determined by the equation:

$$\text{cross } (\%Gas_1, \%Gas_2) = c(\%Gas_1)^{r_1}(\%Gas_2)^{r_2} \qquad \text{Equation 7}$$

where $c$, $r_1$, and $r_2$ are constants that are determined based on a calibration process [the calibration process comprising the application of a plurality (preferably about 5 or more) mixtures of $CO_2$ and $N_2O$ and solving for the constants' values in the above equation], and $\%Gas_1$, and $\%Gas_2$ represent the respective volume percentages of the gas determined. In effect what the above equation reveals is the amount of error in one gas given the presence of a second gas. Therefore, the actual $CO_2$ and $N_2O$ volume percentage values are corrected by further subtracting the channel cross coupling values determined above:

$$\%CO_2 = \phi CO_2 CO_2^{-1}(NRCO_2) - cross(\%CO_2, \%N_2O) \qquad \text{Equation 8a}$$

$$\%N_2O = \phi N_2 ON_2 O^{-1}(NRN_2O) - cross(\%N_2O, \%CO_2) \qquad \text{Equation 8b}$$

Thus, by determining this cross coupling effect, the percent concentration of $CO_2$ and $N_2O$ can then be calculated. Once calculated, these percent concentrations are then converted from percent to mm of Hg values, and are then corrected for the pressure difference between the pressure at calibration and the operating the pressure by using outside pressure sensors (not shown in drawings).

The cross coupling effects that $CO_2$ and $N_2O$ have on the normalized voltage ratios for each of the five agent channels is then removed by dividing out the $CO_2$ and $N_2O$ cross coupling values $[\phi(\%Agent, \%CO_2)\phi(\%Agent, \%N_2O)]$ from the agent normalized ratios which had been previously corrected for secondary thermal compensation to result in a more accurate agent normalized voltage ratio ($NR_{Agent}$):

$$NR_{Agent} = NR_{channel\ corrected} / [\phi(\%Agent, \%CO_2)\phi(\%Agent, \%N_2O)] \qquad \text{Equation 9}$$

Once these corrected agent normalized voltage ratios ($NR_{Agent}$) are obtained, the search for agent types(s) and concentration(s) can begin. The first step in this process is to assume that only one agent exists. The normalized ratios for each of the agents are fed into the inverse (i.e., normalized ratio to volume percentage) equations for each agent:

$$\%Agent = \phi_{AgentAgent}^{-1}(NR_{Agent}) \qquad \text{Equation 10}$$

The resulting values from each equation are then stored for later use in case a dual agent combination was not detected. Next, a search is made for the best fit for two agents out of all ten possible combinations. This is done by calculating the absolute value of the difference between the product of two normalized agent ratios, where $NR_{gas} = \phi_{SensorAgent1Agent2}(\%Agent2)$, and the normalized ratio for a potential second agent as shown below:

$$\text{error}_{SensorAgent1} = |\phi_{SensorAgent1Agent2}(\%Agent2) \cdot \phi_{SensorAgent1Agent3}(\%Agent3) - NR_{SensorAgent1}| \qquad \text{Equation 11}$$

This difference is the amount of error that exists between the actual normalized ratio of an agent channel and the normalized ratio that should exist on that channel for two given volume percentages of agents. In the above equation, Agent1 can be the same agent as Agent2 or Agent1 can be the same agent as Agent3. The subscript on the function $\phi$ is read as "the normalized ration produced by channel Agent1 given an input of Agent2." The errors are collected for each of the five agents channels and then totaled for this two-gas combination. This process is repeated at equally spaced intervals for the valid ranges for each agent. The agent combination with the lowest error is the best fit.

For example, to calculate the total error in a search for isoflurane and sevoflurane, Agent2 would be isoflurane and Agent3 would be sevoflurane. Agent1 is one of the five agents. The total error would then be calculated as:

$$\text{error}_{Des} = |\phi_{DesIso}(\%Iso)|\phi_{DesSevo}(\%Sevo) - NR_{Des}| \qquad \text{Equation 12a}$$

$$\text{error}_{Iso} = |\phi_{IsoIso}(\%Iso)|\phi_{IsoSevo}(\%Sevo) - NR_{Iso}| \qquad \text{Equation 12b}$$

$$\text{error}_{Hal} = |\phi_{HalIso}(\%Iso)|\phi_{HalSevo}(\%Sevo) - NR_{Hal}| \qquad \text{Equation 12c}$$

$$\text{error}_{Enf} = |\phi_{EnfIso}(\%Iso)|\phi_{EnfSevo}(\%Sevo) - NR_{Enf}| \qquad \text{Equation 12d}$$

$$error_{Sevo} = |\phi_{SevoIso}(\%Iso)|\phi_{SevoSevo}(\%Sevo) - NR_{Sevo}| \quad \text{Equation 12e}$$

$$error_{total} = error_{DES} + error_{iso} + error_{Hal} + error_{enf} + error_{Sev} \quad \text{Equation 12f}$$

The smallest total error detected is the best fit found for the isoflurane-sevoflurane combination. A similar search is then performed for the remaining nine combinations of agents. The combination of agent values with the lowest error would then be considered the best dual agent match given the normalized ratios presented to the agent search algorithm. Once a pair of agents is found, the primary agent is declared as the agent with the greatest concentration, the secondary agent is the agent with the lowest concentration. If the primary agent's concentration is below a threshold value, for example 0.2%, then no dual agent combination is considered found. A similar test is performed for the secondary agent. If the secondary agent's percentage volume is below a certain threshold then no secondary agent exists and the value used for the primary agent is the value obtained from the previous single agent calculation. If the single agent's concentration is below a threshold value, 0.1% for example, then no agent is considered found.

The corrected normalized ratios are then used to determine the calibration coefficients/variable $c_1$, $c_2$, and $k$, or $a_0 \ldots a_n$ for equation 13e, of each agent for the following five equations which will be later used to determine the concentration of the interested gas:

$$y = c_1(1-x) \quad \text{Equation 13a}$$

$$y = c_1(e^{c_2(1-x)} - 1) \quad \text{Equation 13b}$$

$$y = c_1(e^{c_2 x} - 1) + 1 \quad \text{Equation 13c}$$

$$y = c_1(e^{c_2(1-xk)} - 1) \quad \text{Equation 13d}$$

$$y = a_n x^n + \ldots + a_1 x + a_0 \quad \text{Equation 13e}$$

With the determination of these calibration coefficients for each channel, the system is now ready to detect and determine the concentrations of carbon dioxide, nitrous oxide, and each of the anesthetic agents in the respiratory gas stream. In the preferred embodiment, the system begins by zeroing each gas to obtain a baseline value. This is done by measuring the voltage across a detector's junction when no anesthetic agent gas is present. Such zeroing can occur at regular or predetermined intervals to help remove the effect of wideband (heating up of the system) and thermal changes in the source heater and the channel filters.

When the baseline detector voltage is needed, a valve is opened which provides fresh air to the agent detectors. The amount of time that fresh air is provided is critical, since the overall temperature of the detector(s) change (slowly) as a secondary thermal effect as the sampled gas infrared absorption varies with the concentration. If too long a time is taken in providing fresh air then the operating temperature of the sensors will change, rendering the baseline voltage values useless. If too short of a time is taken then not all of the agent gases will be purged from the sensor and an invalid baseline voltage value will be recorded. It has been experimentally determined that two seconds of fresh air for the agent channels and four seconds of fresh air for the $CO_2$ and $N_2O$ channels are sufficient to obtain the respective baseline voltage values. These times are dependant upon the volume of the gas stream and volume of the heat flow from the infrared source in the present sample cell design.

Thus, by dividing the voltage across a detector by this baseline voltage, a value is generated that will be one for each gas channel when no agent exists and will become smaller as the agent's volume percentage increases and occludes more infrared radiation. Since any changes in the heater will be common to both the numerator and the denominator, these changes are thus cancelled. This process is referred to as normalization and is used to calculate the normalized voltage ratios as described earlier.

Two type of zeroing are performed: a two second zero for agents only and a four second zero for $CO_2$ and $N_2O$. Two mechanisms exist to trigger a zero. The first is a temporal zero which may be performed at the following intervals after the sensor warms up: 0 minute, 2 minute, 4 minute, 6 minute, 8 minute, 10 minute, 20 minute, 40 minute, and 1 hour. Thereafter, every hour. All temporal zeros are four second zeros.

The second is a conditional zero, which is performed depending upon the state of the agent analysis system. Whenever a conditional zero is performed, the zeroing mechanism will wait for a certain period of time, i.e., 27 seconds, from the time the zero valve closes for the system to stabilize. Once the system stabilizes, the current agent types and concentrations are stored as old values and testing for the conditions shown below in Table I resume, which if detected, will trigger a either a short zeroing (i.e. 2 seconds) or long zeroing (i.e. 4 seconds) of the system:

TABLE I

| Condition Triggering a Zero | Type of Zero |
|---|---|
| The primary agent type changes or the secondary agent type changes. | Short zero. |
| The concentration of $N_2O$ changes by more than 30%. | Long zero. |
| The N20 volume percentage is greater than 10% AND the primary agent OR secondary agent concentrations changes by more than 4%. | Long zero. |
| The current primary OR current secondary agent concentrations are greater than 1.0% AND the last recorded primary OR secondary agents concentrations are greater than 1.0% AND the primary OR secondary agent concentrations change by greater than 400%. | Short zero. |

During the course of the anesthesia, the system detects when a patient breathes. When a breath transition is detected, a 0.3 second average of the normalized ratio values over the inspired or expired regions is used for agent calculations. This averaging reduces the noise in the sensor data to an acceptable level. When no breath is detected for 15 seconds (4 breaths per minute), the agent calculation will not trigger on a breath transition, but will constantly produce agent type/concentration data.

The voltage across the thermopile is sampled for each detector, preferably about every $\frac{1}{30}$ th of a second. As an example, each detector's output may be filtered using a first order, lowpass infrared filter with a 5 rad/sec cutoff frequency and corresponding wavelength/bandwidth given in Table II below:

TABLE II

| Channel Number | Channel Type | Center Wavelength (Microns) | Bandwidth (Microns) |
|---|---|---|---|
| 1 | $CO_2$ | 4.262 | 0.208 |
| 2 | sevoflurane | 10.925 | 0.250 |
| 3 | Isoflurane | 10.000 | 0.190 |
| 4 | Agent Reference | 10.420 | 0.350 |
| 5 | $CO_2/N_2O$ reference | 4.826 | 0.208 |
| 6 | Blocked | All blocked | All blocked |
| 7 | Halothane | 12.275 | 0.250 |
| 8 | Enflurane | 12.950 | 0.400 |

TABLE II-continued

| Channel Number | Channel Type | Center Wavelength (Microns) | Bandwidth (Microns) |
|---|---|---|---|
| 9 | Desflurane | 9.775 | 0.250 |
| 10 | N$_2$O | 4.552 | 0.293 |

Figure 4:
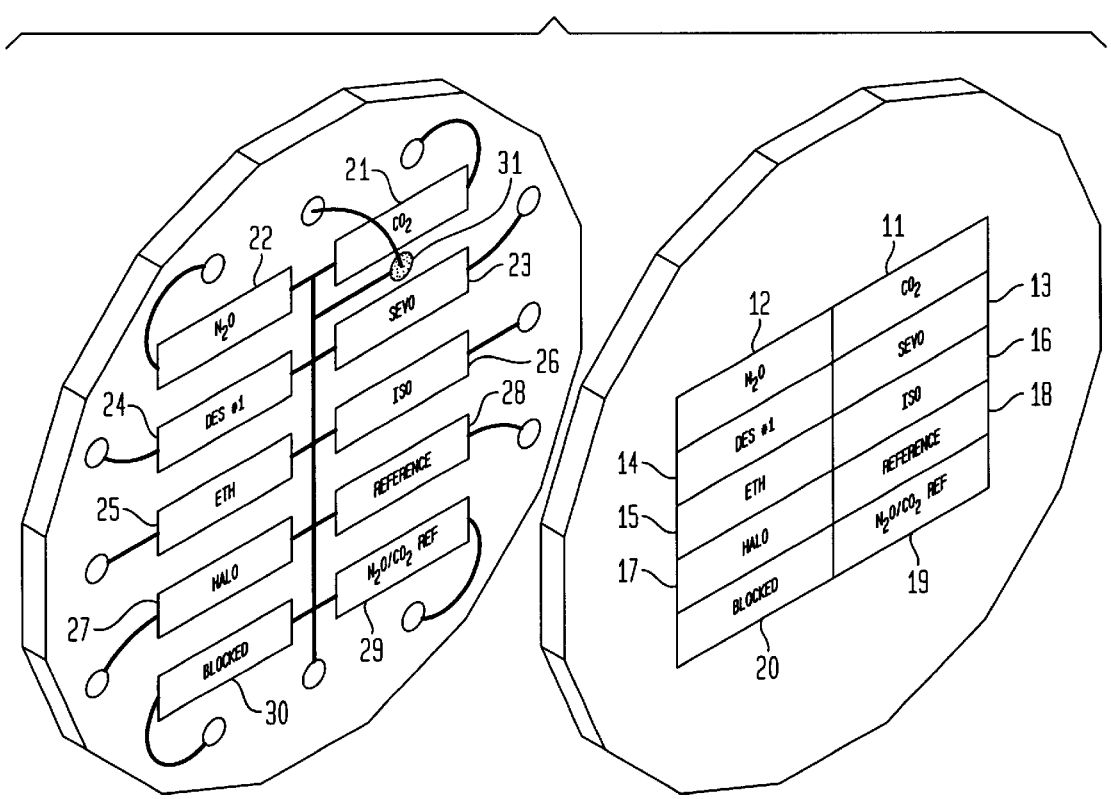
FIG. 4 is a side view of the preferred embodiment illustrating how the ten thermopiles and filter components may be aligned with respect to each other within the infrared detector portion of the gas detection apparatus in accordance with the principles of the present invention.
Figure 5:
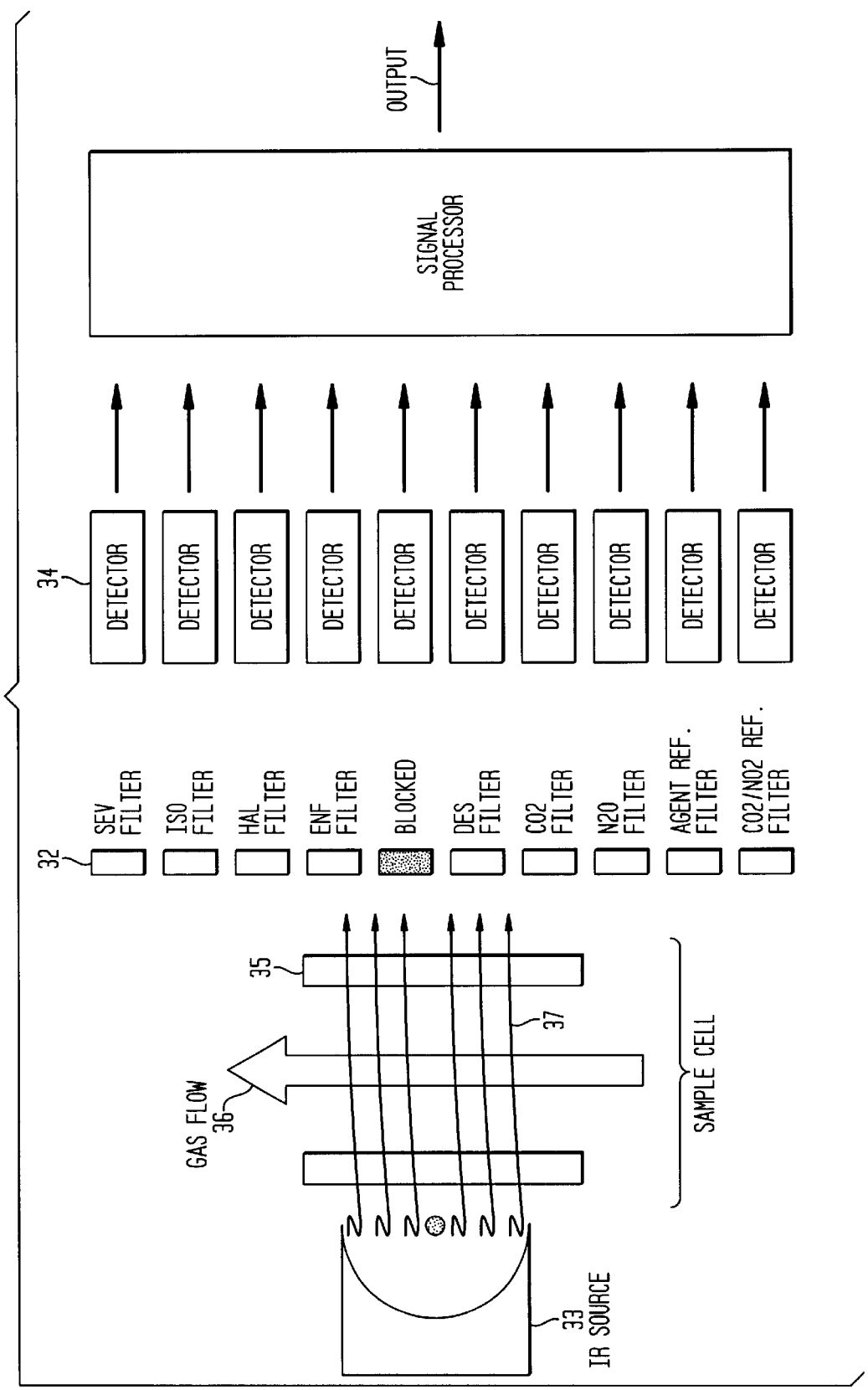
FIG. 5 is an illustration of the path of the infrared light from the infrared source to the infrared detector when used in accordance with the principles of the present invention.
Figure 6:
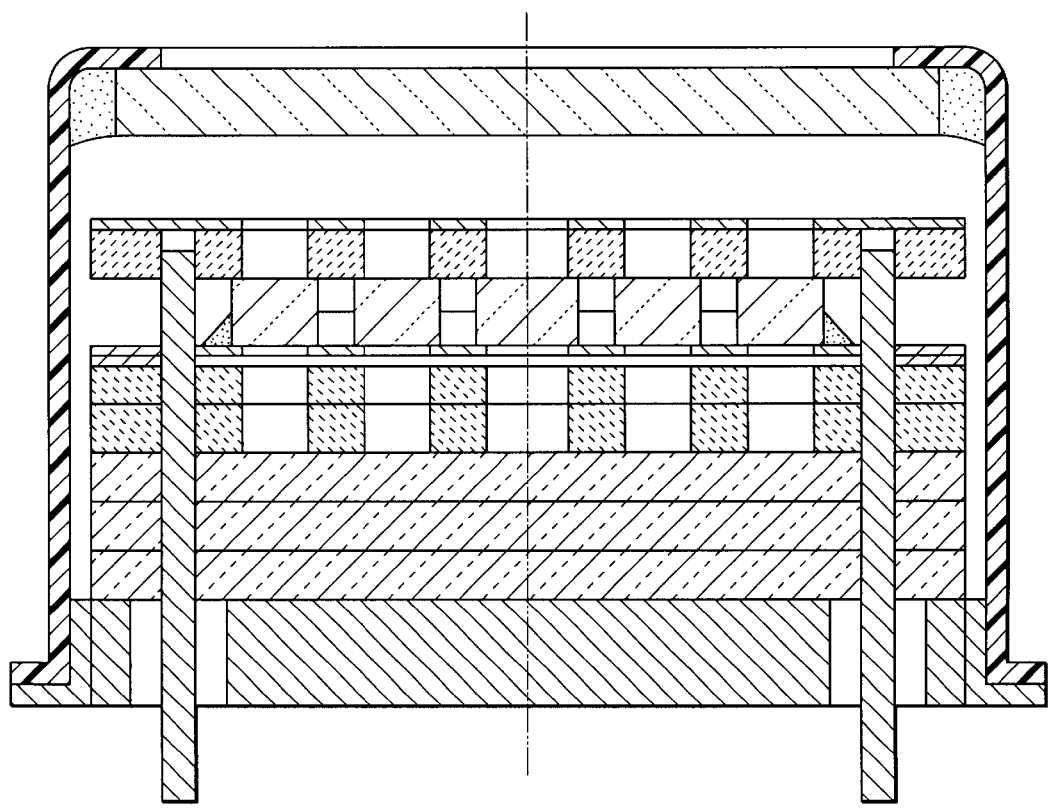
FIG. 6 is a side view of the infrared detector elements of the gas detection apparatus constructed in accordance with the principles of the present invention.

The above channel information can be used as an example of the corresponding thermopile/filter arrangement in FIG. 4. These values are a matter of design choice and empiral experimentation to obtain values that function in the apparatus in the desired manner, which function is also dependent upon the particular filters used. In addition, these values, although shown to nanometers, need not be used with the same degree of precision as shown. Once the voltage readings have been taken, an average ground voltage (V$_{gnd}$) is then calculated $$V_{gnd}=(Vgnd_1+Vgnd_2)/2 \qquad \text{Equation 14}$$

and then subtracted from the ten detector outputs in order to correct for ground offsets.

Throughout this entire process of determining the concentration of the interested gas agent, the system is constantly repeating the calculations discussed earlier using the values derived during the calibration process. Thus, the system will use the scale factor determined from the calibration to perform its primary thermal compensation to determine the voltage of each of the channels. The system will also use the normalized ratios determined during the calibration process to find the normalized ratios, and ultimately the concentration of the unknown gas agent using the above equations as well.

However, this method of detecting an agent and its concentration will only work this easily when no other gases are present that absorb the same wavelengths of infrared radiation and if the bandpass filters used are perfect notch filters for the exact wavelength of infrared radiation that we wish to detect. These conditions are rather ideal since there almost always exist other gases present which absorb infrared radiation that is close to the wavelength or frequency of the interested gas. This overlapping absorption, or interference, as described earlier, is called cross coupling.

In order to solve the problem of cross coupling, measurement of the concentration of the interfering gas is taken and used to correct for any changes in the other agent channels.

This effect of cross coupling must also be corrected in the normalization process. In other words, the normalized voltage ratio for a particular detector must also be divided by the normalized voltage ratio produced by the interfering gas, as described earlier. This calculation is based on the key concept that when two gases absorb infrared radiation at similar wavelengths, the normalized ratio for a detector is the product of the normalized ratios due to each separate gas.

The high frequency components of the gas channels may also be amplified in order to provide sharper inspired-expired breath transitions. Sharper transitions increase the accuracy of the agent calculation functions by providing flatter inspired and expired regions of the waveform over which data can be collected. The weak breath transitions are caused by the time it takes to fill the cavity that surrounds the agent sensor (sample cell). The following equation is used to amplify the high frequency components:

$$y=[x(2A+2W_t)+x_{prev}(W_t-2-2A)+y_{prev}(2-W_t)]/[2+W_t] \qquad \text{Equation 15}$$

where $W_t$ is the filter's cutoff frequency, x is the current sample, $x_{prev}$ is the previous sample, $y_{prev}$ is the previous filter output, and A is the filter's gain. The current value of $W_t$ is 5 radians/second. The current value used for A is determined at calibration time by adjusting A until the flattest inspired and expired waveform regions are obtained.

Although the preferred and specific embodiments of this invention have been shown and described, it should be understood that various modifications and rearrangements of the parts may be resorted to without departing from the scope and spirit of the invention as disclosed and claimed herein. It will be appreciated by those of ordinary skill in these art that the description given herein with respect to those figures is for illustrative purposes only and is not intended in any way to limit the scope of the invention. All questions regarding the scope of the invention may be resolved by referring to the appended claims.

What is claimed is:

1. An apparatus for measuring the concentration of anesthetic gas in a patient's respiratory airstream flowing through a gas conduit comprising:

a source of infrared radiation for illuminating the gas in the conduit;

a plurality of independent infrared detectors for detecting infrared radiation from the gas illuminated in the conduit, each detector further comprising a filter to permit only infrared radiation of a particular wavelength to reach each respective infrared detector;

one or more reference infrared detectors, each detector furtherer comprising a filter to permit only infrared radiation of a particular wavelength to reach each respective reference infrared detector;

at least one blocked infrared detector with an opaque filter to prevent substantially all infrared radiation from reaching said blocked detector infrared detector, the number of blocked infrared detectors being fewer than said plurality of independent infrared detectors; and a processor for correcting each independent infrared detector output by algebraic removal of a scaled version of the output of said reference and said at least one blocked infrared detectors from the output of each independent infrared detector.

2. The apparatus defined in claim 1, wherein said source of infrared radiation provides infrared radiation from 3 to 14 microns.

3. The apparatus defined in claim 2, wherein the infrared radiation source is a black body.

4. The apparatus defined in claim 1, wherein said processing means includes developing normalized ratios corresponding to each independent infrared detector.

5. The apparatus defined in claim 1, wherein said processing means further comprises:

means for measuring and compensating for offset voltage;

means for removing the effect of wide band and thermal changes in the infrared radiation source and each of the bandpass filters; and means for adjusting the modulation level in each infrared detector; and means for correcting the effects of cross coupling.

6. The apparatus defined in claim 1, further comprising:

means for averaging voltages;

means for amplifying high frequency measurements; and means for zeroing the system.

7. The apparatus defined in claim 1, further comprising:

means for determining a baseline voltage value wherein said means include determining an optimum time for exposing fresh air to the infrared detectors; and means for correcting for pressure difference between the pressure at calibration and the operating pressure.

8. The apparatus of claim 1, wherein there is only one blocked detector.

9. A method for calibrating and detecting an anesthetic agent in a patient's respiratory gas stream, comprising the steps of:

providing a source of infrared radiation;

illuminating a patient's respiratory gas stream with infrared radiation;

providing a plurality of independent infrared detectors for receiving the infrared radiation from the illuminated gas stream, each independent detector having a corresponding infrared bandpass filter for each gas or anesthetic agent to be measured;

providing a reference infrared detector for receiving the infrared radiation from the illuminated gas stream, each reference detector having a corresponding infrared bandpass filter;

providing at least one blocked detector infrared detector with a filter opaque to the infrared radiation from the illuminated gas stream, the number of blocked infrared detectors being fewer than said plurality of independent infrared detectors;

measuring the voltage across each infrared detector; and correcting for each independent infrared detector voltage measurement by algebraic removal of a scaled version of the measurement of the reference and the blocked infrared detectors from the output of each separate independent infrared detector.

10. The method defined in claim 9, further comprising the steps of:

measuring and compensating for the effects of offset voltage;

determining a baseline voltage;

determining a normalized ratio for each infrared detector;

compensating for effects of wideband and thermal changes;

compensating for effects of cross coupling;

determining the concentration of the interested gases based on the results of the calibration process; and zeroing the system at predetermined intervals.

11. The method defined in claim 9, further comprising the steps of:

amplifying the high frequency components of the infrared detectors; and improving the modulation of each channel.

12. The method of claim 9, wherein there is only one blocked detector.

13. An apparatus for measuring the concentration of one or more anesthetic gases in a respiratory gas stream, comprising:

a source of infrared radiation;

a plurality of independent infrared detectors, each having a corresponding bandpass filter through which infrared radiation passes to reach each detector;

one or more reference infrared detectors, each having a corresponding bandpass filter through which infrared radiation passes to reach each detector;

at least one blocked detector infrared detector with a filter opaque to infrared radiation and positioned to block infrared radiation that would pass to the detector, the number of blocked infrared detectors being fewer than said plurality of independent infrared detectors;

means for calibrating the system; and means for detecting and determining the concentration of one or more of said anesthetic gases.

14. An apparatus as in claim 13, further comprising:

means for measuring and compensating for the effects of offset voltage;

means for compensating for the effects of thermal drifts or changes; and means for compensating for the effects of cross coupling.

15. The apparatus of claim 13, wherein there is only one blocked detector.

* * * * *